US012697017B2

(12) United States Patent
Maeda

(10) Patent No.: US 12,697,017 B2
(45) Date of Patent: Aug. 4, 2026

(54) IMAGE PICKUP UNIT, ENDOSCOPE, AND MANUFACTURING METHOD OF IMAGE PICKUP UNIT

(71) Applicant: OLYMPUS MEDICAL SYSTEMS CORP., Tokyo (JP)

(72) Inventor: Kazuya Maeda, Tokyo (JP)

(73) Assignee: OLYMPUS MEDICAL SYSTEMS CORP., Tokyo (JP)

(*) Notice: Subject to any disclaimer, the term of this patent is extended or adjusted under 35 U.S.C. 154(b) by 131 days.

(21) Appl. No.: 18/782,733

(22) Filed: Jul. 24, 2024

(65) Prior Publication Data

US 2024/0374125 A1 Nov. 14, 2024

Related U.S. Application Data

(63) Continuation of application No. PCT/JP2022/020350, filed on May 16, 2022.

(51) Int. Cl.
*A61B 1/00* (2006.01)
*A61B 1/05* (2006.01)

(52) U.S. Cl.
CPC .......... *A61B 1/051* (2013.01); *A61B 1/00097* (2022.02); *A61B 1/0011* (2013.01)

(58) Field of Classification Search
CPC ... A61B 1/051; A61B 1/00097; A61B 1/0011; A61B 1/05
See application file for complete search history.

(56) References Cited

U.S. PATENT DOCUMENTS

2011/0118549 A1* 5/2011 Han .......................... A61B 1/04 29/854
2014/0375784 A1* 12/2014 Massetti ............ A61B 1/00097 348/222.1
2015/0216395 A1 8/2015 Stuehle et al.
2017/0251914 A1 9/2017 Kitano
2022/0369918 A1* 11/2022 Toth ................... A61B 1/00114

FOREIGN PATENT DOCUMENTS

EP 3257429 A2 12/2017
JP 2002159438 A 6/2002
JP 3955458 B2 8/2007
JP 2008118568 A 5/2008
JP 4136058 B2 8/2008
JP 2014236475 A 12/2014
JP 2015531246 A 11/2015
JP 2017153769 A 9/2017
JP 6574448 B2 9/2019
WO 2014037069 A1 3/2014

OTHER PUBLICATIONS

International Search Report dated Jul. 26, 2022 received in PCT/JP2022/020350.

* cited by examiner

*Primary Examiner* — Timothy J Neal
(74) *Attorney, Agent, or Firm* — Scully, Scott, Murphy & Presser, P.C.

(57) ABSTRACT

An image pickup unit includes: an image pickup module including an image sensor and a wiring board; a frame within which the image pickup module is housed and fixed; and a motion sensor fixed to an inner surface of the frame.

20 Claims, 8 Drawing Sheets

FIG. 3

IMAGE PICKUP UNIT, ENDOSCOPE, AND MANUFACTURING METHOD OF IMAGE PICKUP UNIT

CROSS REFERENCE TO RELATED APPLICATION

This application is a continuation application of PCT/JP2022/020350 filed on May 16, 2022, the entire contents of which are incorporated herein by this reference.

BACKGROUND OF THE INVENTION

1. Field of the Invention

This invention relates to an image pickup unit having a frame housing an image pickup module and a sensor, an endoscope including the image pickup unit having the frame housing the image pickup module and the sensor, and a manufacturing method of the image pickup unit having the frame housing the image pickup module and the sensor.

2. Description of the Related Art

Endoscopes are used in the medical and industrial fields. Endoscopes have been developed in which electronic components other than an image pickup device are placed in the distal end portion of the insertion portion, to add new functions and enhance performance.

Japanese Patent No. 4136058 discloses an endoscope that uses a gravity sensor placed in the distal end portion of the insertion portion to detect the direction of gravity in the endoscope image being observed.

Japanese Patent No. 6574448 discloses an endoscope that uses a motion sensor placed in the distal end portion of the insertion portion to detect the amount of relative movement with respect to the subject, to thereby control focus.

SUMMARY OF THE INVENTION

An image pickup unit according to an embodiment includes: an image pickup module including an image pickup device and a wiring board; a frame within which the image pickup module is housed and fixed; and a sensor fixed to an inner surface of the frame.

In an endoscope according to an embodiment, an image pickup unit is provided in a distal end portion of an insertion portion to be inserted into a subject. The image pickup unit includes: an image pickup module including an image pickup device and a wiring board; a frame within which the image pickup module is housed and fixed; and a sensor fixed to an inner surface of the frame.

A manufacturing method of an image pickup unit according to an embodiment includes: fixing a sensor to an inner surface of a frame; housing an image pickup module within the frame; and fixing the image pickup module to the frame.

A manufacturing method of an image pickup unit according to an embodiment includes: fixing a sensor to a first member that is substantially plate-shaped; housing and fixing an image pickup module within a second member that is frame-shaped and has a notch; and fixing the first member to the second member so that the first member covers the notch of the second member and the sensor is housed within the second member.

BRIEF DESCRIPTION OF THE DRAWINGS

FIG. 3 is an exploded perspective view of the image pickup unit according to the first embodiment.

DETAILED DESCRIPTION OF THE PREFERRED EMBODIMENTS

First Embodiment

Figure 1:
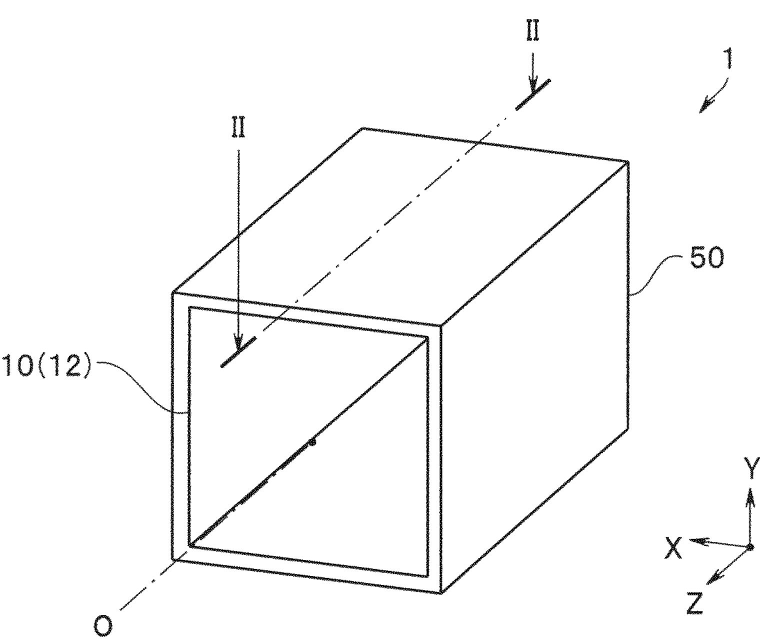
FIG. 1 is a perspective view of an image pickup unit according to a first embodiment.
Figure 2:
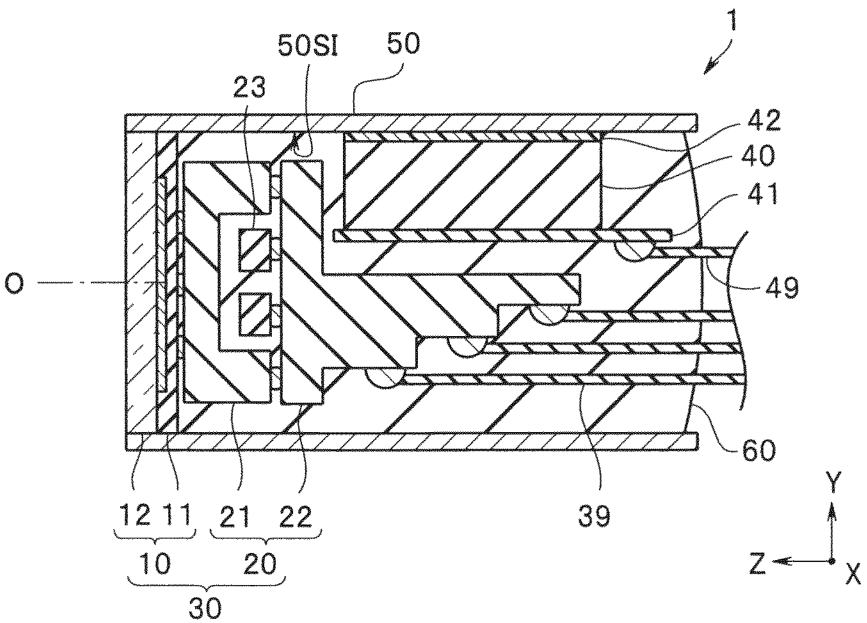
FIG. 2 is a cross-sectional view taken along line II-II in FIG. 1.
Figure 3:
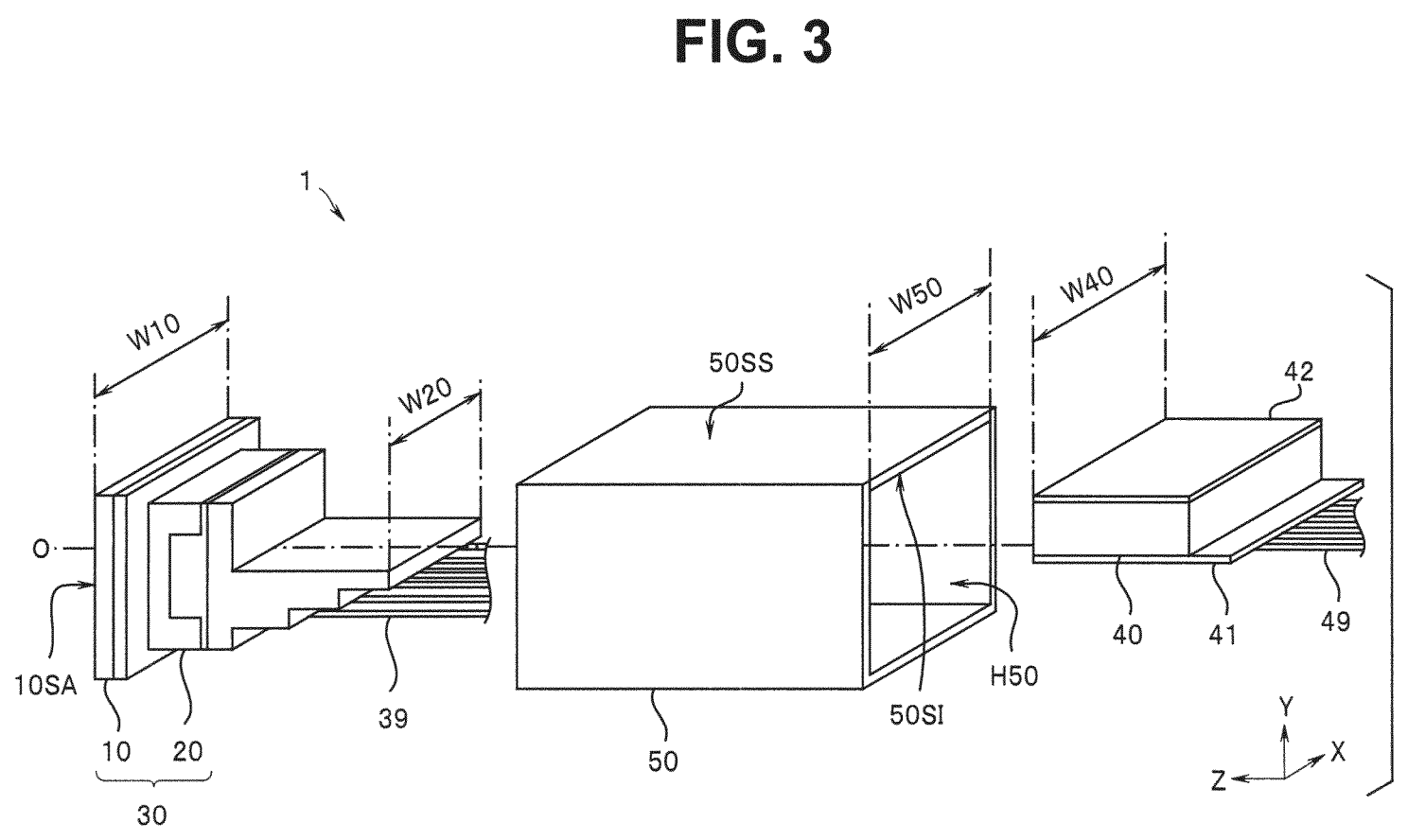

An image pickup unit 1 according to the embodiment shown in FIGS. 1, 2 and 3 includes an image pickup module 30, a motion sensor 40, and a frame 50. The image pickup module 30 is housed within the frame 50 and fixed to the frame 50. The motion sensor 40 is fixed to an inner surface 50S1 of the frame 50.

The drawings based on the embodiment are schematic. The relationship between the thickness and width of each part and the ratio of the thickness of each part differ from the actual object. The drawings also contain parts in which dimensional relationships and ratios are different from each other. The direction of the subject is referred to as "front" and the opposite direction to "front" as "rear."

The image pickup module 30 has an image sensor 10, a wiring board 20, and a cable 39. The image sensor 10 includes an image pickup device 11 and a cover glass 12. The image pickup device 11 converts a subject image incident through the cover glass 12 into an electrical signal. The image pickup device 11 may be either of the front-surface irradiation type or the rear-surface irradiation type. Although not shown, an image pickup optical system including a plurality of lenses is disposed in front of the cover glass 12 of the image sensor 10.

The wiring board 20 has a first wiring board 21 and a second wiring board 22. The first wiring board 21 is, for example, a three-dimensional ceramic wiring board formed by stacking a plurality of ceramic wiring layers. The ceramic wiring board is fabricated by stacking a plurality of unfired ceramic sheets (green sheets), each having a surface wiring and a through-hole wiring, and subsequently firing the stacked ceramic sheets. The first wiring board 21 has a recess in a rear surface bonded to a front surface of the second wiring board 22.

The front surface of the second wiring board 22 has a plurality of electronic components 23, such as chip capacitors, that are surface mounted on the front surface. The plurality of electronic components 23 are housed in the recess in the rear surface of the first wiring board 21. A cable 39 is bonded to a bottom surface orthogonal to the front surface of the second wiring board 22. The second wiring board 22, which is an irregularly shaped wiring board, is a ceramic wiring board, a composite wiring board to which a plurality of flat wiring boards are bonded, or a molded interconnect device (MID).

The wiring board 20 may be configured by only one of the first wiring board 21 and the second wiring board 22. In other words, the image pickup module 30 may not have two wiring boards.

A motion sensor 40 is a 6-axis IMU (Inertial Measurement Unit) consisting of a 3-axis acceleration sensor and a 3-axis gyro sensor. The acceleration sensor measures acceleration and the gyro sensor measures angular velocity. The motion sensor 40 has a movable member like a cantilever.

When a motion sensor was deformed by the effect of stress applied from outside, it used to be that the detection accuracy decreases, leading to deteriorated reliability. In general, the bigger the motion sensor, the higher the sensitivity. However, an image pickup units having a big motion sensor is big.

The frame 50 is made of, for example, a cylindrical copper sheet with a thickness of 50 μm to 100 μm. Inner and outer corners of the cylinder may be chamfered. The frame 50 protects the image pickup module 30 and has a shielding effect to block electromagnetic fields from the outside.

The motion sensor 40 is fixed to an inner surface 50SI of the frame 50 using an adhesive 42. A flexible wiring board 41 is bonded to an external electrode (not shown) of the motion sensor 40. A cable 49 is bonded to the wiring board 41.

The image sensor 10 transmits and receives electrical signals using a cable 39. The motion sensor 40 transmits and receives electrical signals using the cable 49.

A sealing resin 60 is disposed within the frame 50. The sealing resin 60 is an epoxy resin, an ABS resin, a silicone resin, a polyimide resin, a BCB (benzocyclobutene) resin, or the like.

As shown in FIG. 3, in the image pickup unit 1, in an X direction, which is one direction parallel to a light receiving surface 10SA of the image sensor 10, an outer dimension W40 of the motion sensor 40 is larger than an outer dimension W20 of the wiring board 20. An inner dimension W50 of the frame 50 is larger than an outer dimension W10 of the image sensor 10 and the outer dimension W40 of the motion sensor 40.

A sensor with a large outer dimension is more sensitive than a sensor with a small outer dimension. However, the motion sensor 40 has the outer dimension W40 that is larger than the outer dimension W20 of the wiring board 20, and thus may not be mounted on the wiring board 20.

Even if the motion sensor 40 is mountable on the wiring board 20, mounting the big motion sensor 40 on the wiring board 20 may make it impossible to house the image pickup unit in the frame 50. This is caused by bonding errors in the manufacturing of the image pickup unit.

Two facing and bonded surfaces of the image pickup unit are ideally parallel. However, in reality, the two surfaces are not parallel due to a bonding error. In an image pickup unit having a plurality of bonding locations, bonding errors are added up.

The image pickup unit 1 has three bonding surfaces: a bonding surface between the image sensor 10 and the first wiring board 21; a bonding surface between the first wiring board 21 and the second wiring board 22; and a bonding surface between the wiring board 20 and the motion sensor 40.

Figure 4:
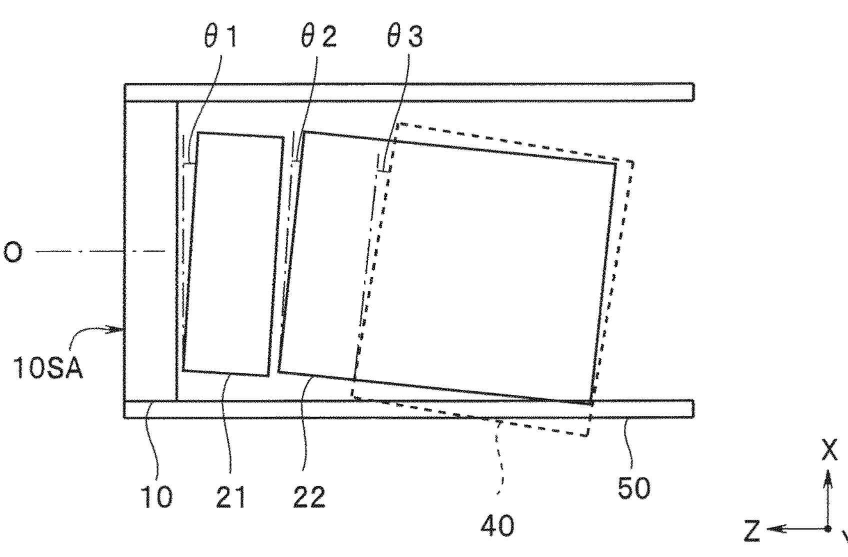
FIG. 4 is a schematic top view to illustrate the bonding accuracy of the image pickup unit.

As shown in FIG. 4, the bonding surface between the image sensor 10 and the first wiring board 21 has a bonding error of angle θ1. The bonding surface between the first wiring board 21 and the second wiring board 22 has a bonding error of angle θ2. Furthermore, when the sensor is placed on the wiring board 20, there is an error of angle θ3. In the worst case, a rear surface of the motion sensor 40 is inclined by an angle (θ1+θ2+θ3) with respect to the light receiving surface 10SA of the image sensor 10. For this reason, when mounted on the wiring board 20, the motion sensor 40 may not able to be housed in the frame 50.

In contrast to this, if the outer dimension W40 of the motion sensor 40 is smaller than the inner dimension W50 of the frame 50, the motion sensor 40 can certainly be housed in the frame 50 in the image pickup unit 1 in which the motion sensor 40 is adhered to the frame 50.

The image pickup unit 1 includes the motion sensor 40 that is big and highly sensitive, and therefore has high performance. In addition, the image pickup unit 1 does not need to increase an outer dimension of the frame 50 to account for the bonding errors.

Having at least two bonding surfaces yields that the effect of the invention is remarkable. In other words, even if the first wiring board 21 and the second wiring board 22 are in the form of an integral wiring board, the image pickup unit in which the motion sensor 40 is adhered to the frame 50 has the effect of the present invention even if the bonding errors are combined.

<Manufacturing Method of Image Pickup Unit>

Figure 5:
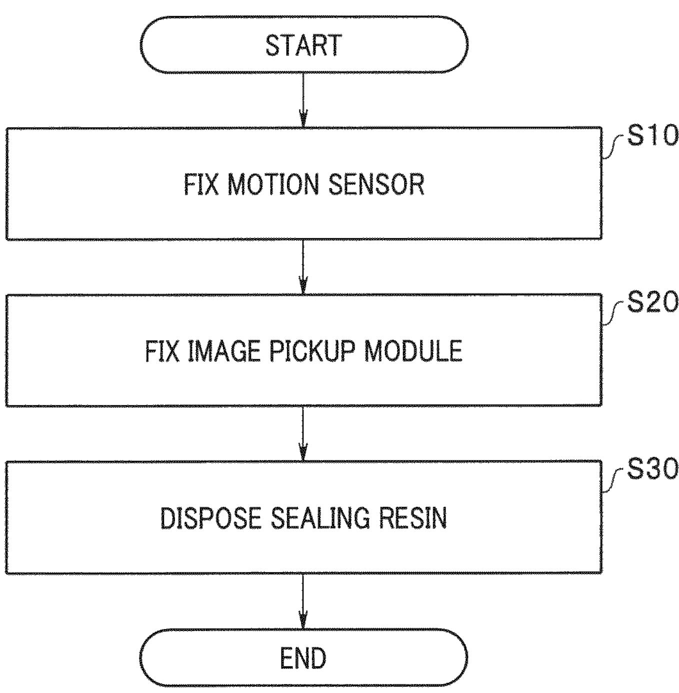
FIG. 5 is a flowchart of a manufacturing method of the image pickup unit according to the first embodiment.

A manufacturing method of the image pickup unit 1 is briefly described in line with the flowchart of FIG. 5.

<Step S10> Fixing Process of Motion Sensor

The motion sensor 40 is manufactured using MEMS technology that simultaneously forms a large number of movable parts like cantilevers, piezoelectric elements that detect changes in the movable parts, or the like, on a silicon wafer for bulk manufacturing. The motion sensor 40 may be a physical quantity detection sensor such as an acceleration sensor, a gyro sensor, or a temperature sensor. The effect of the present invention is particularly noticeable when the motion sensor 40 is a sensor having a movable part that is susceptible to stress and is for detecting a physical quantity.

Figure 6A:
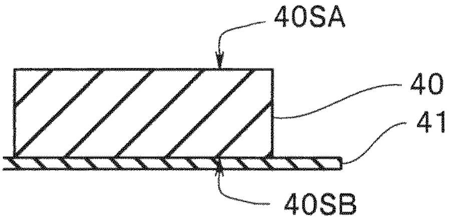
FIG. 6A is a cross-sectional view to illustrate the manufacturing method of the image pickup unit according to the first embodiment.

As shown in FIG. 6A, the wiring board 41 is bonded to a bottom surface 40SB on which an external electrode (not shown) of the motion sensor 40 is placed. The wiring board 41 is, for example, a flexible wiring board having a polyimide substrate.

Figure 6B:
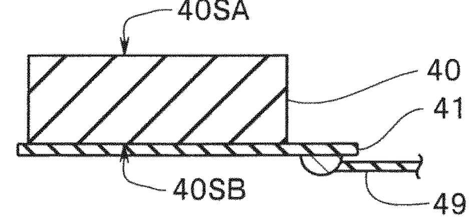
FIG. 6B is a cross-sectional view to illustrate the manufacturing method of the image pickup unit according to the first embodiment.

As shown in FIG. 6B, the cable 49 is bonded to the flexible wiring board 41.

Figure 6C:
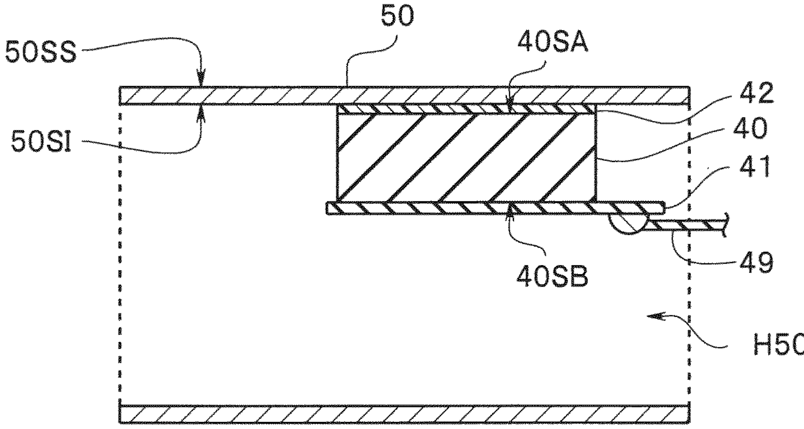
FIG. 6C is a cross-sectional view to illustrate the manufacturing method of the image pickup unit according to the first embodiment.
Figure 6D:
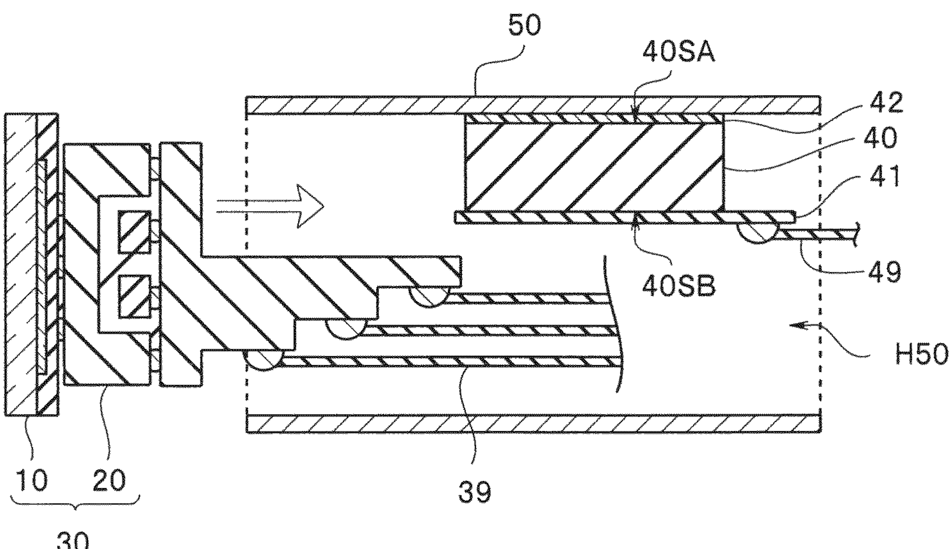
FIG. 6D is a cross-sectional view to illustrate the manufacturing method of the image pickup unit according to the first embodiment.

As shown in FIG. 6C, a top surface 40SA of the motion sensor 40 is fixed to an inner surface 50S1 of the frame 50 using an adhesive 42. The inner dimension W50 of the frame 50 is set to be slightly larger than the outer dimension W40 of the motion sensor 40.

For example, for miniaturization of the image pickup unit, the inner dimension W50 is preferably less than 105% and sometimes preferably less than 102% of the outer dimension W40. For example, when the outer dimension of the motion sensor 40 is 5 mm, the inner dimension W50 of the frame 50 is preferably less than 5.25 mm and particularly preferably less than 5.1 mm.

<Step S20> Fixing Process of Image Pickup Module

The image sensor 10 is fabricated, for example, by adhering a glass wafer to an image pickup wafer having a light-receiving circuit consisting of CCD or CMOS, and subsequently cutting the bonded wafer. In the image sensor 10, one or more semiconductor devices that process the image pickup signals may be stacked on the rear surface of the image pickup device 11.

The first wiring board 21 and the second wiring board 22 are fabricated. The electronic components 23, such as chip capacitors, are surface mounted on the second wiring board 22. The first wiring board 21 and the second wiring board 22 are bonded so that the electronic components 23 are housed in the recess of the first wiring board 21, thus forming the wiring board 20. The wiring board 20 and the image sensor 10 are bonded to each other and the cable 39 is bonded to the wiring board 20, thus forming the image pickup module 30.

The image pickup module 30 is fixed to the frame 50. The outer dimension W10 of the image sensor 10 is slightly smaller than the inner dimension W50 of the frame 50. Thus, the image sensor 10 is fitted and fixed into the frame 50. An adhesive may be disposed on a side surface of the image sensor 10 to fix the image sensor 10 to the frame 50.

<Step S30> Resin Sealing Process

Filling the sealing resin 60 in a hollow portion H50 of the frame 50 completes the image pickup unit 1 shown in FIG. 2.

According to this manufacturing method, the motion sensor 40 has the outer dimension W40 that is larger than the outer dimension W20 of the wiring board 20, but is housed within the frame 50.

Modifications of First Embodiment

Because image pickup units 1A-1D according to first to fourth modifications of the first embodiment are similar to and have the same effects as the image pickup unit 1, the same reference numerals are attached to components with the same functions and descriptions thereof are omitted.

First Modification of First Embodiment

Figure 7:
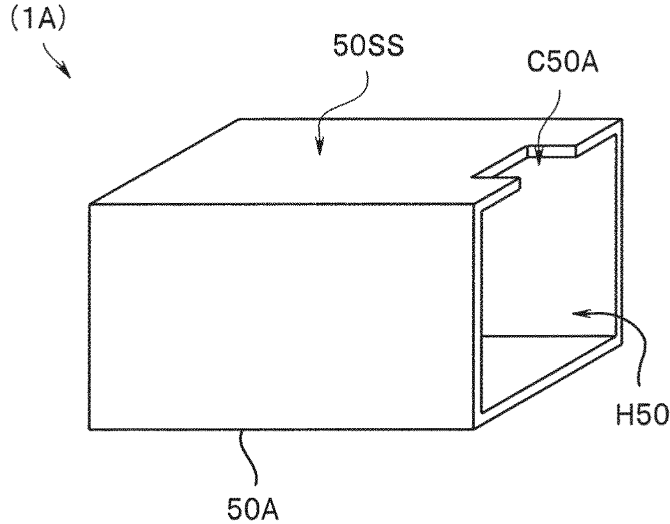
FIG. 7 is a perspective view of a frame of the image pickup unit according to a modification of the first embodiment.

FIG. 7 shows a frame 50A of an image pickup unit 1A according to this modification. The frame 50A has a notch C50A in a side surface 50SS to which the motion sensor 40 is to be adhered. Therefore, positioning of the motion sensor 40 is easy when fixing the motion sensor 40 to the frame 50A. For example, a position where a rear end portion of the motion sensor 40 inserted from the rear into the hollow H50 of the frame 50A coincides with a front end of the notch C50A is set as the placement position of the motion sensor 40.

Second Modification of First Embodiment

Figure 8:
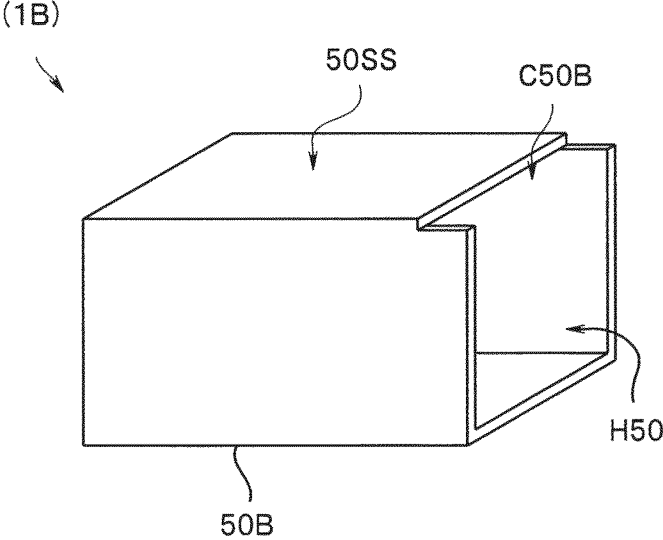
FIG. 8 is a perspective view of the frame of the image pickup unit according to the modification of the first embodiment.

FIG. 8 shows a frame 50B of an image pickup unit 1B according to this modification. In the frame 50B, a notch C50B is formed by notching the entirety of a single side surface 50SS. In other words, the side surface 50SS is shortened in length in a direction of an optical axis O by the notch C50B. As with the image pickup unit 1A, in the image pickup unit 1B, positioning of the motion sensor 40 is easy when fixing the motion sensor 40 to the frame 50B.

Third Modification of First Embodiment

Figure 9:
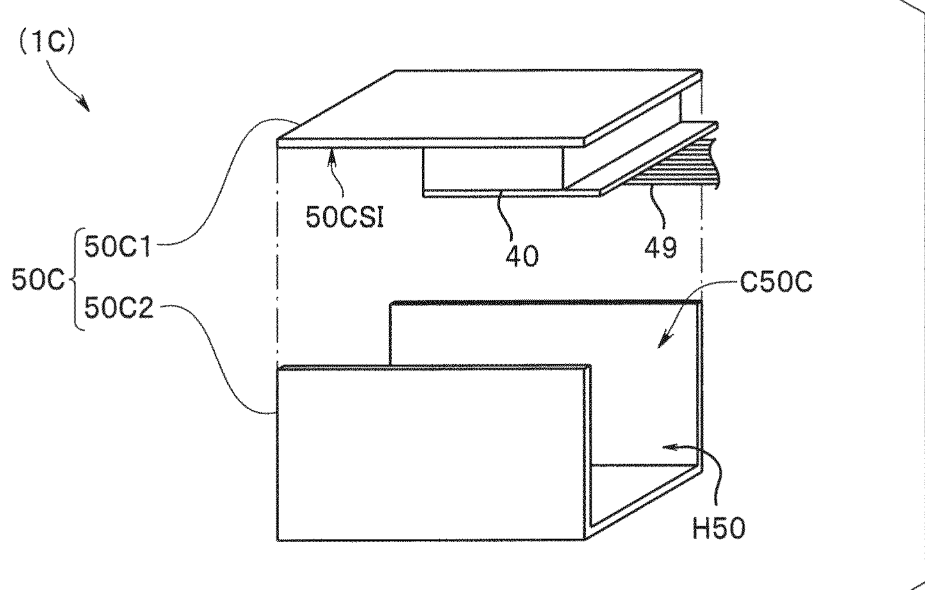
FIG. 9 is a perspective view to illustrate the manufacturing method of the image pickup unit according to the modification of the first embodiment.

FIG. 9 is an exploded view of a frame 50C of the image pickup unit 1C according to this modification. The frame 50C is configured by a first member 50C1 and a second member 50C2. The first member 50C1 is plate-shaped. The second member 50C2 is a frame that has a top surface having a notch, and that has a substantially U-shaped cross section orthogonal to the optical axis O. The first member 50C1 is fixed to the second member 50C2 using an adhesive or a solder so that the bottom surface 50CSI covers the notch of the second member 50C2.

The motion sensor 40 is fixed to the first member 50C1. Although not shown, the image pickup module is placed on the second member 50C2.

A manufacturing method of the image pickup unit 1C of the third modification includes: a process of fixing the motion sensor 40 to the bottom surface 50CSI of the first member 50C1 that is substantially plate-shaped; a process of housing and fixing an image pickup module within the second member 50C2 that is frame-shaped and has a notch C50C; and a process of fixing the first member 50C1 to the second member 50C2 so that the first member 50C1 covers the notch C50C of the second member 50C2 and the motion sensor 40 is housed within the second member 50C2.

It is easier to place the motion sensor 40 at a predetermined position on the first member 50C1 that is a flat plate than to place the motion sensor 40 on the inner surface 50SI of the frame 50. Therefore, the image pickup unit 1C is easier to manufacture than the image pickup unit 1.

Fourth Modification of First Embodiment

Figure 10:
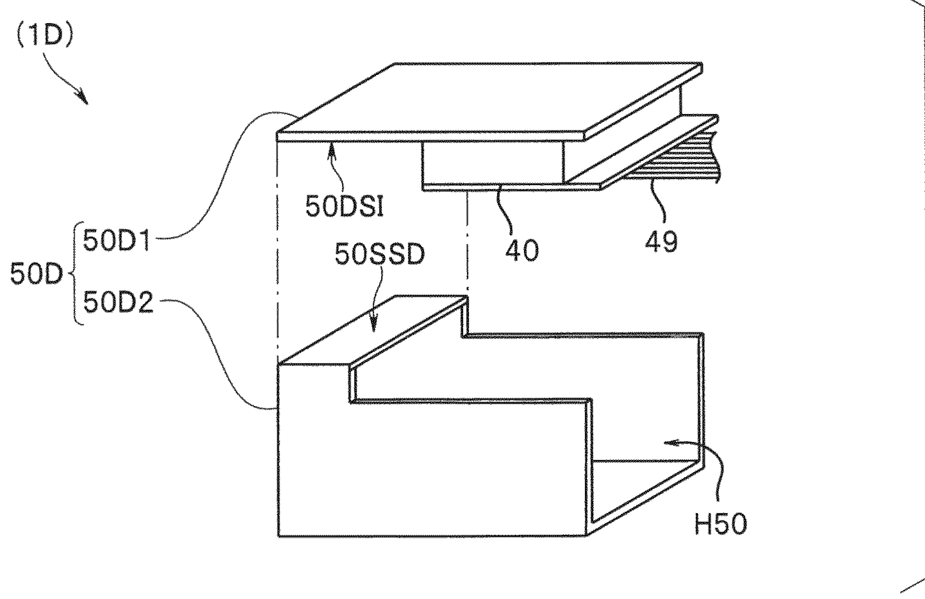
FIG. 10 is a perspective view to illustrate the manufacturing method of the image pickup unit according to the modification of the first embodiment.
Figure 11:
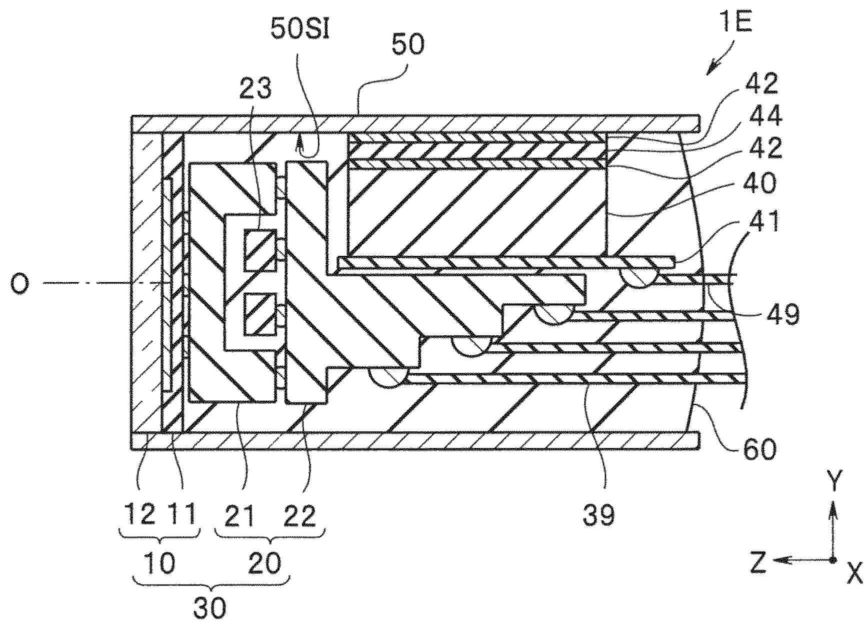
FIG. 11 is a cross-sectional view of an image pickup unit according to a modification of a second embodiment.

FIG. 10 is an exploded view of a frame 50D of the image pickup unit 1D according to this modification. The frame 50D is configured by a first member 50D1 and a second member 50D2. The first member 50D1 is plate-shaped. The second member 50D2 is a frame-shaped member that has an upper surface 50SSD, part of which has a notch, and that has a substantially U-shaped cross section orthogonal to the optical axis O. The first member 50D1 is fixed to the second member 50D2 to cover the notch of the second member 50D2.

In the image pickup unit 1D, the frame 50D is fabricated by adhering a bottom surface 50DSI of the first member 50D1 that is a flat plate to the top surface 50SSD, which is unnotched, of the second member 50D2. The image pickup unit 1D has the effect of the image pickup unit 1C, and furthermore, it is easy to fix the first member 50D1 and the second member 50D2.

Second Embodiment

Because an image pickup unit 1E according to this embodiment is similar to and has the same effects as the image pickup unit 1, the same reference numerals are attached to components with the same functions and descriptions thereof are omitted.

The image pickup unit 1E further includes a protection plate 44 that is more rigid than the frame 50 between the frame 50 and the motion sensor 40. The protection plate 44 is fixed to the inner surface 50SI of the frame and to the motion sensor 40 by the adhesive 42 on the top and bottom, respectively, of the protection plate 44.

Rigidity is a characteristic that prevents shape change when stress is applied from outside. In this specification, "rigidity" is defined as the product of Young's modulus and thickness of the material that configures a member. Young's modulus (modulus of elasticity) was measured at 25° C. according to ASTM-D638.

For example, the frame 50 is made of aluminum with a Young's modulus of 70 GPa and has a thickness of 100 μm. In contrast, the protection plate 44 is made of alumina with a Young's modulus of 370 GPa and has a thickness of 100 μm.

In the image pickup unit 1E having the protection plate 44, the frame 50 is hardly deformed even when stress is applied to the frame 50. For this reason, the motion sensor 40 is not easily deformed even when stress is applied to the frame 50, and thus the accuracy of the motion sensor 40 does not deteriorate.

Third Embodiment

Figure 12:
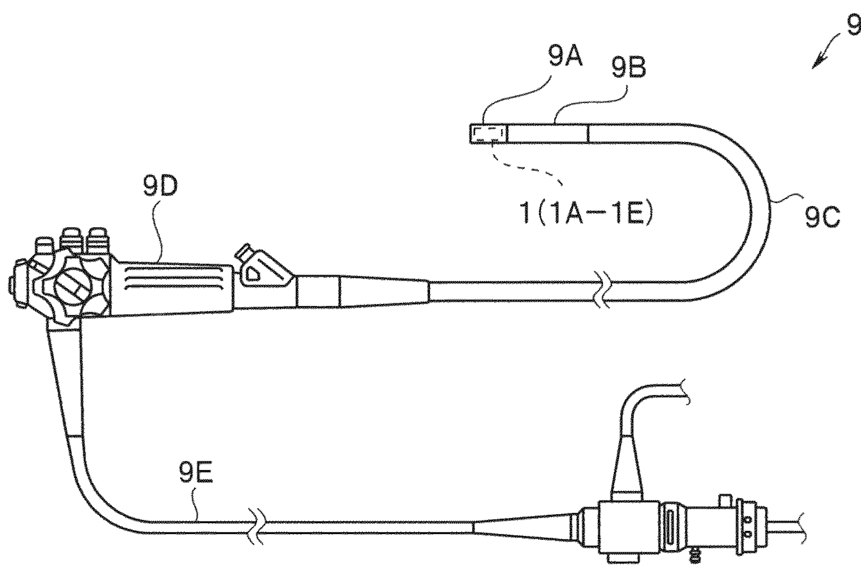
FIG. 12 is an external view of an endoscope according to a third embodiment.

FIG. 12 shows an endoscope 9 of this embodiment.

The endoscope 9 includes an insertion portion to be inserted into a subject and having: a rigid distal end portion 9A in which the image pickup unit 1 (1A-1E) is disposed; a bendable bending portion 9B continuously connected to a proximal end of the rigid distal end portion 9A; and an elongated flexible portion 9C continuously connected to a proximal end of the bending portion 9B. The bending portion 9B is bent by operating an operation portion 9D. A universal cord 9E extended from the operation portion 9D is connected to a processor or the like, which is not shown.

The endoscope 9 has the image pickup unit 1 (1A-1E) thereby yielding high performance, and has stable operation thereby yielding high reliability.

Note that the endoscope 9 is a flexible endoscope for medical purpose, but an endoscope of another embodiment may be an endoscope for industrial purpose, or a rigid endoscope having a rigid straight tube instead of a flexible portion 90C.

The present invention is not limited to the above-mentioned embodiments, and the like, and various changes, modifications, and the like can be made within a scope not changing the gist of the invention.

What is claimed is:

1. An image pickup unit comprising:
an image pickup module including an image sensor and a wiring board;
a frame within which the image pickup module is housed and fixed; and
a motion sensor fixed to an inner surface of the frame;
wherein in one direction parallel to a light receiving surface of the image sensor, an outer dimension of the motion sensor is larger than an outer dimension of the wiring board, and
the wiring board comprises a first wiring board bonded to a rear surface of the image sensor and a second wiring board bonded to a rear surface of the first wiring board.

2. The image pickup unit according to claim 1, wherein the frame has a notch in a side surface to which the motion sensor is fixed.

3. The image pickup unit according to claim 1, further comprising:
a protection plate that is more rigid than the frame,
wherein the protection plate is disposed between the frame and the motion sensor.

4. The image pickup unit according to claim 1, wherein the frame includes a first member to which the motion sensor is fixed and a second member on which the image pickup module is placed.

5. The image pickup unit according to claim 4, wherein
the second member having a notch, and
the first member is plate-shaped and is fixed to the second member to cover the notch.

6. An endoscope comprising:
an insertion portion configured to be inserted into a subject, and
the image pickup module according to claim 1 disposed in a distal end of the insertion section.

7. The image pickup unit according to claim 1, wherein the image sensor comprises a cover glass.

8. The image pickup unit according to claim 1, further comprising a sealing resin disposed within the frame.

9. The image pickup unit according to claim 1, wherein one or more of the first wiring board and the second wiring board being only connected to the motion sensor via the sealing resin.

10. The image pickup unit according to claim 1, wherein the frame has a rectangular cross-section in a direction perpendicular to a light receiving direction of the image pickup module.

11. An image pickup unit comprising:
an image pickup module including an image sensor and a wiring board;
a frame within which the image pickup module is housed and fixed;
a motion sensor fixed to an inner surface of the frame; and
a protection plate that is more rigid than the frame,
wherein the protection plate is disposed between the frame and the motion sensor.

12. The image pickup unit according to claim 11, wherein
in one direction parallel to a light receiving surface of the image sensor, an outer dimension of the motion sensor is larger than an outer dimension of the wiring board, and
the wiring board comprises a first wiring board bonded to a rear surface of the image sensor and a second wiring board bonded to a rear surface of the first wiring board.

13. The image pickup unit according to claim 11, wherein the frame has a notch in a side surface to which the motion sensor is fixed.

14. The image pickup unit according to claim 11, wherein the frame includes a first member to which the motion sensor is fixed and a second member on which the image pickup module is placed.

15. The image pickup unit according to claim 14, wherein
the second member is a frame-shaped member having a notch, and
the first member is plate-shaped and is fixed to the second member to cover the notch.

16. An endoscope comprising:
an insertion portion configured to be inserted into a subject, and
the image pickup module according to claim 11 disposed in a distal end of the insertion section.

17. The image pickup unit according to claim 11, wherein the image sensor comprises a cover glass.

18. The image pickup unit according to claim 11, further comprising a sealing resin disposed within the frame.

19. The image pickup unit according to claim 11, wherein one or more of the first wiring board and the second wiring board being only connected to the motion sensor via the sealing resin.

20. The image pickup unit according to claim 11, wherein the frame has a rectangular cross-section in a direction perpendicular to a light receiving direction of the image pickup module.

* * * * *